United States Patent [19]

Bowen

[11] Patent Number: 4,659,751

[45] Date of Patent: Apr. 21, 1987

[54] SIMPLIFIED METHOD FOR OBTAINED STRONG ADHESIVE BONDING OF COMPOSITES TO DENTIN, ENAMEL AND OTHER SUBSTRATES

[75] Inventor: Rafael L. Bowen, Gaithersburg, Md.

[73] Assignee: American Dental Association Health Foundation, Washington, D.C.

[21] Appl. No.: 825,319

[22] Filed: Feb. 3, 1986

Related U.S. Application Data

[63] Continuation-in-part of Ser. No. 699,079, Feb. 7, 1985, which is a continuation-in-part of Ser. No. 516,956, Jul. 25, 1983, Pat. No. 4,521,550, which is a continuation-in-part of Ser. No. 457,029, Jan. 10, 1983, Pat. No. 4,514,527.

[51] Int. Cl.$^4$ .................. A10N 1/02; A65K 3/00; C09K 3/00

[52] U.S. Cl. .................. 523/116; 106/35; 260/998.11; 424/147; 433/228.1

[58] Field of Search .................. 433/228.1; 523/116, 523/115, 114; 106/35; 424/147; 260/998.11

[56] References Cited

U.S. PATENT DOCUMENTS

| | | | |
|---|---|---|---|
| 3,200,142 | 8/1965 | Bowen | 106/35 |
| 3,635,889 | 1/1972 | Bowen | 106/35 |
| 3,785,832 | 1/1974 | Bowen | 106/35 |
| 4,148,988 | 4/1979 | Mashuara et al. | 106/35 |
| 4,150,012 | 4/1979 | Joos | 260/998.11 |
| 4,251,565 | 2/1981 | Bowen | 433/226 |
| 4,486,179 | 12/1984 | Brauer et al. | 106/35 |
| 4,514,527 | 4/1985 | Bowen | 106/35 |
| 4,521,550 | 6/1985 | Bowen | 106/35 |
| 4,524,824 | 6/1985 | Shimokobe et al. | 106/35 |
| 4,535,102 | 8/1985 | Kusumoto et al. | 433/228.1 |
| 4,536,523 | 8/1985 | Antonucci | 433/228.1 |
| 4,544,467 | 10/1985 | Bunker et al. | 433/228.1 |
| 4,548,583 | 10/1985 | Smith et al. | 433/228.1 |
| 4,572,920 | 2/1986 | Rawls et al. | 523/116 |
| 4,579,880 | 4/1986 | Ohashi et al. | 523/116 |

FOREIGN PATENT DOCUMENTS

1448134  9/1976  United Kingdom ................ 106/35

OTHER PUBLICATIONS

Bowen, R. L., "Composite and Sealant Resins—Past, Present, and Future", *Pediatric Dentistry*, The American Academy of Pododontics, vol. 4, No. 1, 1982, pp. 10–15.

Plueddemann, E. P., "Mechanism of Adhesion Through Silane Coupling Agents", *Coposite Materials*, 1974, vol. 6, pp. 173–216, publisher: Academic Press, N.Y.

Nakabayashy, Nobuo; Masuhara, Eiichi, "Preparation of Hard Tissue Compatible Materials: Dental Polymers", *Biomedial Polymers, Polymeric Materials and Pharmaceuticals for Biomedical Use*, Institute for Medical and Dental Engineering, Tokyo Medical and Dental University, Tokyo, Japan, pp. 85–111.

Misra, D. N.; and Bowen, R. L., "Adhesive Bonding of Various Materials to Hard Tooth Tissues XII. Adsorption of N-(2-Hydroxy-3-Methacryloxypropyl)-N--Phenyl-glycine (NPG-GMA) on Hydroxyapatite," *Journal of Colloid and Interface Science*, vol. 61, No. 1, Aug. 1977, pp. 14–20.

Misra, D. N. and Bowen, R. L., "Adsorption of N-(-2-hydroxy-3-methacryloxypropyl)-N-phenylglycine (NPG-GMA) on Cupric Ion-Enriched Hydroxyapatite Surface to Improve Chemical Bonding Between Dental Resins and Teeth", *Biomaterials*, 1981, vol. 2, Apr., pp. 78–82.

Palit, S. R. and Koner, R. S., "Permanganate-Oxalic Acid as a Redox Initiator in Aqueous Media," 57 *J. Polymer Sci.* 609–615 (1962).

Bowen, R. L., Cobb, E. N.; and Rapson, J. E., "Adhesive Bonding of Various Materials to Hard Tooth Tissues: Improvement in Bond Strength to Dentin", *J. Dent. Res.* 61(9): 1070–1076, Sep. 1982.

Bowen, R. L. and Cobb, E. N., "A Method for Bonding to Dentin and Enamel", *JADA*, vol. 107, Nov. 1983.

Lal, et al., "New Polymerization Catalysts for Methyl Methacrylate," 24 *J. Polym. Sci.* 75–84 (1957).

Uehara "Polymerization of Methyl Methacrylate Initiated by a Combined Action of Trichloracetic Acid and Dimethylaniline," 31 *Bull. Chem. Soc. Jap.* 685–687 (1958).

Hrabak, et al., "The Initiation of Polymerization of Unsaturated Tertiary Amines with Carboxylic Acids," 182 *Macromol. Chem.* 1595–1603 (1981).

Bowen, R. L., "Adhesive Bonding of Various Materials to Hard Tooth Tissues. I. Method of Determining Bond Strength," 44 J. Dent. Res. 690–695 (1965).

(List continued on next page.)

*Primary Examiner*—Ronald W. Griffin
*Attorney, Agent, or Firm*—Allegretti, Newitt, Witcoff & McAndrews, Ltd.

[57] ABSTRACT

Materials and methods for improving the adhesion of composite materials and resins to dentin, enamel and other substrates are disclosed. Preferably, the substrate surface is treated with an aqueous solution of (1) at least one acid (preferably nitric acid), (2) at least one polyvalent cation (preferably an aluminum cation) which can bind to dentin or enamel, and (3) at least one compound (preferably oxalic acid) which forms relatively water-insoluble precipitates with calcium and with polyvalent cations at pH values above that of the acidic treatment solution, and (4) a composition preferably comprising N-phenylglycine and/or other amino acids. Then, a solution is applied which contains at least one compound selected from the group consisting of (1) the addition reaction product of pyromellitic acid dianhydride and 2-hydroxyethyl methacrylate ("PMDM"), (2) the addition reaction product of 3,3',4,4'-benzophenonetetracarboxylic dianhydride and 2-hydroxyethyl methacrylate ("BTDA-HEMA"), (3) 4-methacryloxyethyltrimellitic anhydride ("4-META"), and (4) other monomers. Alternative embodiments are also set forth.

46 Claims, No Drawings

OTHER PUBLICATIONS

Bowen, R. L., "Investigation of the Surfaces of Hard Tooth Tissues by a Surface Activity Test," in Phillips, R., & Ryge, G. (eds.): *Proceedings of the Workshop on Adhesive Restorative Dental Materials* 177–191 at Indiana University, Sep. 28–29, 1961, Spencer, Indiana: Owen Litho Service.

Bowen, R. L., "Development of an Adhesive Restorative Material," in *Adhesive Restorative Dental Materials II* 225–231, University of Virginia Workshop, Public Health Service Publication No. 1494, (Washington, D.C.: U.S. Government Printing Office, 1966).

Sax, N. I. *Dangerous Properties of Industrial Materials* 715 (1957).

Dwyer, F. & Mellor, D., *Chelating Agents and Metal Chelates* 311 (1964).

Sneed, M. & Maynard, J., *General Inorganic Chemistry* 1080 (1942)*.

Bowen, R. L., "Adhesive Bonding of Various Materials to Hard Tooth Tissues. V. The Effect of a Surface-Active Comonomer on Adhesion to Diverse Substrates," 44 *J. Dent. Res.* 1369–1373 (1965).

Plueddemann, E., *Interfaces in Polymer Matrix Composites* 200 (1974)*.

Jedrychowski, et al., "Influence of a Ferric Chloride Mordant Solution on Resin-Dentin Retention," 60 J. Dent. Res. 134–138 (1981).

Bowen, R. L., "Adhesive Bonding of Various Materials to Hard Tooth Tissues. II. Bonding to Dentin Promoted by a Surface-Active Comonomer," 44 *J. Dent. Res.* 895–902 (1965).

Bowen, R. L., "Adhesive Bonding of Various Materials to Hard Tooth Tissues. III. Bonding to Dentin Improved by Pretreatment and the Use of a Surface-Active Comonomer," 44 *J. Dent. Res.* 903–905 (1965).

Bowen, R. L., "Adhesive Bonding of Various Materials to Hard Tooth Tissues. IV. Bonding to Dentin, Enamel, and Fluorapatite Improved by the Use of a Surface-Active Comonomer," 44 *J. Dent. Res.* 906–911 (1965).

Bowen, R. L., "Adhesive Bonding of Various Materials to Hard Tooth Tissues. XXII. The Effects of a Cleanser Mordant, & PolySAC on Adhesion Between a Composite Resin and Dentin," 59 *J. Dent. Res.,* 809–814 (1980).

Bowen, R. L., "Adhesive Bonding of Various Materials to Hard Tooth Tissues. XIX. Solubility of Dentinal Smear Layer in Dilute Acid Buffers," 28 *Int'l Dent. J.* 97–104 (1978).

Bowen, R. L., "Adhesive Bonding of Various Materials to Hard Tooth Tissues. VII. Metal Salts as Mordants for Coupling Agents," in Moskowitz, H.: Ward, G.; & Woolridge, E., (eds.); *Dental Adhesive Materials,* 205–221, Proceedings from Symposium held Nov. 8–9, 1973 at the Hunter-Bellevue School for Nursing, New York City, Prestige Graphic Services (1974).

SIMPLIFIED METHOD FOR OBTAINED STRONG ADHESIVE BONDING OF COMPOSITES TO DENTIN, ENAMEL AND OTHER SUBSTRATES

This invention was supported in part by USPHS Research grant DE-05129 to the American Dental Association Health Foundation from the National Institute of Dental Research, Bethesda, MD.

This application is a continuation-in-part of co-pending application Ser. No. 699,079, filed Feb. 7, 1985, which is in turn a continuation-in-part of co-pending application Ser. No. 516,956, filed July 25, 1983, now U.S. Pat. No. 4,521,550, which is in turn a continuation-in-part of co-pending application Ser. No. 457,029, filed Jan. 10, 1983, now U.S. Pat. No. 4,514,527.

BACKGROUND OF THE INVENTION

1. Field of the Invention

This invention relates to simplified methods of improving adhesive bonding of acrylic resins to industrial, natural, and dental substrates, and more particularly to dental restoration methods and methods of improving adhesion of composite dental materials to dentin and enamel. More specifically, methods for strong adhesive bonding of composite resins to dentin and enamel are disclosed with the objects of improving treatment of cervical erosions, root caries, potential dental decay, fractures, and other dental conditions and of eliminating much mechanical cutting of dentin and enamel now required for retention of restorations. The complete disclosures of U.S. Pat. No. 4,514,527 and U.S. Pat. No. 4,521,550 and allowed U.S. patent application Ser. No. 699,079, filed Feb. 7, 1985, are expressly incorporated herein by reference.

2. Description of the Prior Art

For many years, advances in the study of methods of adhesive bonding of composite materials to hard tooth tissues have evolved by small increments. Previous experiments in adhesive bonding of composite materials to dentin demonstrated beneficial effects from cleansers, mordants, and adhesion promoting coupling agents; see, for example, Bowen, R. L., "Adhesive Bonding of Various Materials to Hard Tooth Tissues. XXII. The Effects of a Cleanser, Mordant, and PolySAC on Adhesion Between a Composite Resin and Dentin," 59 *J. Dent. Res.* 809–814 (1980); Bowen, R. L., "Use of Polyfunctional Surface-Active Comonomer and Other Agents to Improve Adhesion Between a Resin or Composite Material and a Substrate," U.S. Pat. No. 4,251,565, February 1981; Bowen, R. L., "Adhesive Bonding of Various Materials to Hard Tooth Tissues. XIX. Solubility of Dentinal Smear Layer in Dilute Acid Buffers," 28 *Int'l Dent. J.* 97–104 (1978); Bowen, R. L., "Adhesive Bonding of Various Materials to Hard Tooth Tissues. VII. Metal Salts as Mordants for Coupling Agents," in Moskowitz, H.; Ward, G.; & Woolridge, E., (eds.); *Dental Adhesive Materials* 205–221, Proceedings from Symposium held Nov. 8–9, 1973 at the Hunter-Bellevue School for Nursing, New York City, Prestige Graphic Services (1974).

The rationale for using a surface-active comonomer as a coupling agent to improve bonding has been supported by previous data. Bowen, R. L., "Adhesive Bonding of Various Materials to Hard Tooth Tissues. II. Bonding to Dentin Promoted by a Surface-Active Comonomer," 44 *J. Dent. Res.* 895–902 (1965); Bowen, R. L., "Adhesive Bonding of Various Materials to Hard Tooth Tissues. III. Bonding to Dentin Improved by Pretreatment and the Use of a Surface-Active Comonomer," 44 *J. Dent. Res.* 903–905 (1965); Bowen, R. L., "Adhesive Bonding of Various Materials to Hard Tooth Tissues. IV. Bonding to Dentin, Enamel, and Fluorapatite Improved by the Use of a Surface-Active Comonomer," 44 *J. Dent. Res.* 906–911 (1965); Bowen, R. L., "Adhesive Bonding of Various Materials to Hard Tooth Tissues V. The Effect of a Surface-Active Comonomer on Adhesion to Diverse Substrates," 44 *J. Dent. Res.* 1369–1373 (1965). The addition reaction product of N-phenylglycine and glycidyl methacrylate (NPG-GMA) and the addition reaction product of N-phenylglycine and p-chlorophenyl glycidyl ether (NPG-CGE) are disclosed, respectively, as vehicles to improve adhesive bonding to a limited extent in Bowen, U.S. Pat. No. 3,200,142, Aug. 10, 1965, and in Bowen, British Pat. No. 1,448,134 and U.S. Pat. No. 3,785,832, Jan. 15, 1974.

Although an acid-etch technique has been effective in beneficiating the bonding of composite and unfilled resins to enamel of teeth, no method has existed for achieving strong adhesive bonding between composite and unfilled resins and dentin. Many investigators have been attempting to achieve significantly enhanced adhesive bonds to both dentin and enamel and various other substrates for well over twenty-five years without adequate success.

SUMMARY OF THE INVENTION

The present invention comprises alternative materials and simplified methods which give strong adhesive bonds between composite materials or resins and dentin and also result in effective bonding between these materials or resins and enamel and other natural or industrial substrates with greater color stability of the resultant materials then previously achieved. Thus, it is an advantage of this invention to provide better material and methods that make it easier to obtain aesthetic adhesive bonding of composite and unfilled resins of the type polymerized by free radicals to dentin, enamel, industrial substrates, and/or other substrates containing or capable of binding metallic ions (i.e., ions of elements on the left side and in the center of the periodic table). The resulting products are also within the scope of the invention.

Briefly, the simplified method of the invention is preferably accomplished by a two-step technique which comprises first treating the surface to be bonded with an acidic solution preferably containing nitric or other strong acid, polyvalent cations, and compounds such as oxalic acid or other polyfunctional acids which can form relatively water-insoluble precipitates with calcium and other polyvalent cations at pH values above that of the acidic aqueous treatment solution, and also containing at least one compound selected from the group consisting of (1) N-phenylglycine ("NPG"), (2) the adduct of N(p-tolyl)glycine and glycidyl methacrylate ("NTG-GMA"), (3) the addition reaction product of N-phenylglycine and glycidyl methacrylate ("NPG-GMA"), and (4) other amino acids. Secondly, a solution is applied which contains at least one monomeric compound selected from the group consisting of (1) the addition reaction product of pyromellitic acid dianhydride and 2-hydroxyethyl methacrylate ("PMDM"), (2) the addition reaction product of 3,3',4,4'-benzophenonetetracarboxylic dianhydride and 2-hydroxyethyl methacrylate ("BTDA-HEMA"), and (3) 4-methacryloxyethyltrimellitic anhydride ("4-META").

Alternatively, but less preferred, in the case of vital dentin, the surface to be treated may be contacted with a strongly acid solution, but still containing NPG, NTG-GMA, NPG-GMA, and/or other amino acids; followed by contacting with PMDM, BTDA-HEMA and/or 4-META monomer solution. Also, an acidic solution and the NPG or other amino acid solution can be applied separately, one after the other (instead of as a combined solution), before the PMDM or other monomer is applied. The components for practicing the method of the invention may be conveniently made available in the form of a kit or article of manufacture.

In one embodiment of the invention, it has been discovered recently that the presence of nitric acid in the first aqueous treatment solution in the absence of ferric oxalate results in high bond strengths for the bonding of composite materials and resins to dentin and enamel. An aqueous solution of nitric acid is contacted with the surface of the dentin or enamel, after which the surface is washed and dried. Subsequent to washing and drying the surface, a solution of NPG, NTG-GMA and/or NPG-GMA in acetone is contacted with the surface. Any excess of the NPG, NTG-GMA, or NPG-GMA is removed by the application of clean acetone which is then removed before it evaporates, and the surface is dried. An acetone solution of PMDM, BTDA-HEMA and/or 4-META is then applied. Finally, the surface of the dentin or enamel is dried. The surface is then ready for application of a composite or dental resin which, upon hardening, will adhere to the substrate surface.

In a preferred embodiment of the invention, it has been discovered more recently that NPG and/or other amino acids can be combined in an aqueous nitric acid solution, and this one solution applied in place of the first and second treatment solutions of the above method. An acetone solution of PMDM, BTDA-HEMA and/or 4-META is then applied. One advantage of NPG is that it is widely commercially available. It is used commercially in the preparation of synthetic indigo blue, which is employed for dyeing denims. Another advantage of NPG is that it is not vulnerable to premature polymerization during synthesis or storage, either pure or in solutions, because it does not contain monomeric moieties (methacrylate groups). The acidic NPG solution is best stored in and dispensed from anaerobic containers.

A particularly preferred method of the invention is accomplished by treating the surface of the dentin, enamel or other substrate containing or capble of binding metallic ions with a solution which contains (1) at least one salt of a polyvalent cation which can bind to substrate surface sites; (2) a compound which contains at least one acid group and preferably two or more acidic groups; (3) a strong acid; and (4) at least one surface-active compound selected from the group consisting of NPG, alpha or beta amino acids, and other compounds each of which contain at least one of each of the following groups: carboxyl and amino. The surface-active compound may be a surface-active comonomer which contains a moiety capable of free radical polymerization as well as the carboxyl and amino groups. The resultant substrate surface is then treated with a solution which contains at least one compound selected from the group consisting of (1) PMDM, (2) BTDA-HEMA, (3) 4-META, (4) other compounds containing at least one group or moiety capable of free radical polymerization, and at least one aromatic ring or moiety containing electron-withdrawing substituents which do not interfere with free radical polymerization, and which compound preferably also contains one or more free carboxyl groups, or anhydride groups which can form free carboxyl groups upon hydrolysis, and (5) camphoroquinone.

DESCRIPTION OF PREFERRED EMBODIMENTS

The Most Highly Preferred Embodiments of the Invention as Simplified

This aspect of the invention comprises improved materials and simplified methods for providing strong adhesion of composite materials and resins to dentin and enamel. The invention also comprises the resultant products. The terms "composite material" and "composite resin" are used herein to refer to materials which contain fillers and which can polymerize or harden by a free radical mechanism. "Resins" refers to monomers (or their polymers) without significant filler content. Typical examples include methacrylates, acrylates, and polyesters.

The most preferred inventive method for preparing the substrate surface for adhesion of composite materials and resins comprises contacting the surface with two solutions, one after the other. The first solution comprises (1) at least one or more polyvalent cations (preferably $Al^{3+}$) which can form relatively water-insoluble precipitates with phosphate ions; (2) a compound with at least one carboxyl group and preferably two or more carboxyl groups which can form relatively insoluble precipitates with calcium and other polyvalent cations at pH values above that of the acidic treatment solution; (3) a strong acid; and (4) an amino acid.

The most preferred polyvalent cation was discovered to be the trivalent aluminum ion in dental applications where aesthetics is important in view of the possibility that ferric ion can lead to staining by reduction to ferrous ion in the presence of sulfide. The latter can be generated by the metabolic activity of anaerobic microorganisms. Sulfide does not form black complexes with aluminum ions under conditions of interest.

It was also discovered empirically that aluminum oxalate is soluble in water when formulated with the other ingredients of the present invention. Although literature references list aluminum oxalate as insoluble in water, it was discovered that aluminum oxalate is soluble in water, depending upon stoichiometry and pH. Aluminum oxalate does not precipitate from the aqueous solution of the present invention. Aluminum ions can be expected to form insoluble, metastable, microporous, quasi-amorphous precipitates of phosphate as the aqueous solution reacts with dentin and enamel surfaces. Aluminum ions can also be expected to strengthen the altered substrate surface structures by crosslinking and reinforcing the collagenous component of dentin surface reacted upon by the first aqueous solution of the present invention. In applications where color stability and aesthetics are not deciding factors, aluminum ions, ferric ions, and other polyvalent cations can be used separately or in combinations in the first aqueous solution of the present invention. An important function of the precipitation of one or more polyvalent cations with phosphate ions and/or collagenous and/or organic components is thought to be the occluding or obturating of dentinal tubules in vital dentin so as to protect the odontoblasts and pulpal tissues from ingress of foreign matter.

The function of the optional incorporation of a compound with one or more carboxyl groups, such as, for example, oxalic acid, or an "oligocarboxylic acid" as exemplified hereinbelow, is believed to be the precipitation of insoluble calcium and other complexes which also can assist in obturating the dentinal tubules of vital dentin when it is treated with the first aqueous solution of the present invention.

The acid which is also preferably present in the first aqueous treatment solution renders the solution low in pH. The purpose of the low pH is to dissolve the smeared (disturbed) surface layer on cut dentin, enamel, or other substrates; to partially decalcify intertubular dentin; to remove pellicle, plaque, or other surface contaminants from the substrate; and to "acid etch" enamel and other substrate surfaces. Another function of the strong acid component which renders the first aqueous solution strongly acidic (low in pH) is to provide solubility of some or all of the other components in the aqueous solution. The most preferred acid for use in the inventive method is nitric acid, ranging in concentration from 0.068 to 50% by weight, preferably, 0.1% to 10% by weight and most preferably on the order of about 2 to 5% by weight of the aqueous solution. It has been discovered that compounds such as Al(NO$_3$)$_3$ can hydrolyze in the aqueous formulation of the first solution to provide the strong acid and necessary low pH. Strong acids other than nitric, for example, phosphoric acid, hydrochloric acid, perchloric acid, sulfuric acid and others, may or may not be effective in improving the bond strengths obtainable in the use of the present invention.

The fourth solute in the first solution of the most preferred embodiment comprises at least one compound containing at least one amino group and at least one carboxyl group, such as an amino acid, typified by N-phenylglycine, which is rendered soluble in water because of the low pH of the solution. Presumably the protons form a cationic, water-soluble salt of the amono acid increasing its hydrophilicity to the extent of rendering it soluble in water or at least soluble in the aqueous formulation of solution 1. Although the purpose and function of the amino acid in the present invention has not been ascertained, it appears to play an important role in obtaining the highest bond strengths. It may be speculated that it is surface-active, forms complexes with cations, adsorbs on the nascent surfaces formed within the substrate structures, and plays a role (perhaps by autoxidation and the concomitant formation of free radicals) in the initiation of polymerization of polymerizable compounds applied to the substrate surface subsequently. Because of the known susceptibility of N-phenylglycine and related amino acids to deteriorate in the presence of air, it is important that the first aqueous solution be stored and applied from anaerobic dispensing containers, such as, for example, cartridges, capsules, cylindeers, or vials.

Additional examples of compounds containing at least one amino group and at least one carboxyl group include: the amino acids in general, N-phenylglycine, N(p-toly)glycine, N-phenylalanine, sarkosine, N-lauroylsarkosine, glycine, N,N-dimethylglycine, 3(N-phenyl)amino propionic acid, 3(N-p-tolyl)amino propionic acid, omega-amino fatty acids, N-substituted-omega-amino fatty acids, the addition reaction product of N-phenyl glycine and glycidyl reagents, and the reaction product of N(substituted phenyl)glycine and glycidyl reagents.

Various examples of effective concentrations of the four ingredients in the first aqueous solution are given in Table 1. For example, one effective solution listed has a composition of 5.4% N-phenylglycine dissolved in water which contained two moles of aluminum nitrate plug three moles of oxalic acid for each 5.4 moles of N-phenylglycine.

NPG (N-phenylglycine) is available commercially. NPG is of the following formula:

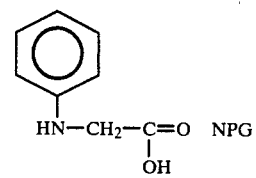

Other suitable related amino acids are compounds containing at least one amino group and at least one carboxyl group and which include members of the following generic structural formula:

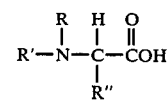

where: R may be aromatic, e.g., phenyl, p-tolyl, etc.; aliphatic, e.g., methyl, ethyl, hydroxyethyl, carboxymethyl, etc.; or hydrogen, preferably phenyl or tolyl; R' may be selected from the same group as R and may be the same as or different from R, preferably hydrogen or methyl; R" may be selected from the same group as R and may be the same as or different from R; preferably methyl or hydrogen.

It has been discovered that EDTA is also effective when employed in the first treatment solution and then followed by NPG and PMDM, etc., and it is believed that related "amino acids", as defined hereinbelow, having the following generic structural formula would also be efficacious:

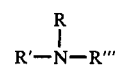

where: R''' is selected from the group:

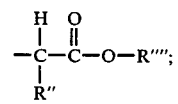

R'''' is selected from the group: H, Na, K, and readily-hydrolyzable lower alkyl and aryl groups; R" is selected from the group: H, CH$_3$, lower alkyl, aryl, and substituted aryl groups; R is selected from the group: phenyl, substituted phenyl, H, lower alkyl, —CH$_2$—

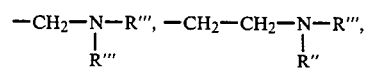

hydroxyethyl, $$-CH_2-CH_2-N-CH_2-CH_2-O-H$$
$$\phantom{-CH_2-CH_2-}|\phantom{CH_2-CH_2-O-H}$$
$$\phantom{-CH_2-CH_2-}R'''$$

and R'''; R' is selected from the group:

$$-CH_2-CHOH-CH_2-O-\underset{\underset{O}{\|}}{C}-\underset{\underset{CH_3}{|}}{C}=CH_2,$$

$$-CH_2-CHOH-CH_2-O-\underset{\underset{O}{\|}}{C}-\underset{\underset{H}{|}}{C}=CH_2,$$

R''', and $$-CH_2-CH_2-\underset{\underset{R'''}{|}}{\overset{\overset{R}{|}}{N}}-R''',$$

and may be the same as or different from R.

After the first aqueous solution has been applied to the substrate surface for a period of time between 1 and 300 seconds, preferably about 60 seconds, it is removed by a forceful stream of compressed air applied for 1 to 30 seconds, preferably between 5 and 10 seconds. Optionally the solution can be washed away with a stream of clean water followed by the application of the compressed air stream.

The second of the two solutions is then applied to the treated substrate surface. The solvent of the second solution is a volatile water-miscible solvent, preferably acetone. The solutes in the second solution are comprised of coupling agents selected from one or more of the following:

$$X\underset{E}{\overset{A}{\underset{(COOH)_g}{\bigcirc}}}\underset{\underset{\underset{O}{\|}}{C}}{\phantom{X}}\left(\underset{(COOH)_g}{\overset{A}{\underset{E}{\bigcirc}}}X\right)_y$$

where:
g=0 to 7, preferably 1;
E is a polymerizable moiety:

$$-(COO-(CH-((CH_3)_jH_k))_q(CHOH)_m-CH_2-)_pOCO-(C-(CH_3)_rH_s)=CH_2;$$

wherein
r=0 or 1, preferably 1;
s=0 or 1, preferably 0;
p=0 to 12, preferably 1;
m=0 to 6, preferably 0;
q=0 to 2, preferably 1;
j=0 or 1, preferably 0;
k=1 or 0, preferably 1;
p+m+q=2 to 20, preferably 2;
the number of E groups per molecule is 1 to 8, preferably 2;
A is an anhydride group —OCOCO— (attached to vicinal ring carbon atoms); the number of A groups per molecule is 0 to 1, preferably 0 or 1;
X is a halide group; and the number of X groups per molecule is 0 to 8, preferably 0; and
y is 0 to 10, preferably 0.

For the purposes of this invention, the term "coupling agents" is expressly defined to mean the compounds of the general formula set forth above.

Of the possible species encompassed within this generic formula, the most preferred is PMDM, the addition reaction product of pyromellitic acid dianhydride and 2 moles of 2-hydroxyethyl methacrylate. While the structure(s) of PMDM are not definitely known, and it is best characterized as the above-recited addition reaction product, the structures of the two isomers of PMDM are postulated to be as follows:

PMDM

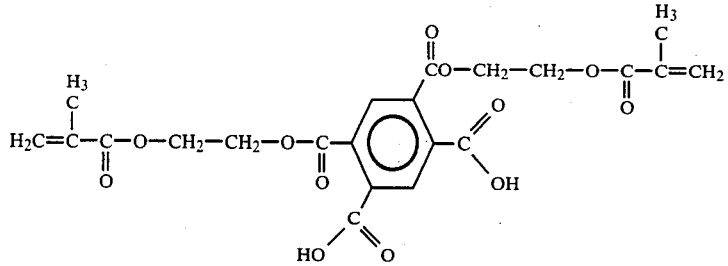

Although the isomer melting at about 163° C. gave bond strengths slightly higher than did the isomer melting at 153° C., they were both effective individually and when admixed. The PMDM isomers may be applied to the dentin or enamel surface in any desired proportions, dissolved in a solvent or a mixture of solvents. Again, the preferred solvent is acetone, although other solvents may be used. A 5% solution of PMDM in acetone is efficacious, although other concentrations, preferably in the range of about 0.1% to a saturated solution, may be used.

PMDM can be used alone, mixed with BTDA-HEMA, or substituted by the use of BTDA-HEMA. BTDA-HEMA is the addition reaction product of 3,3',4,4'-benzophenonetetracarboxylic dianhydride and 2 moles of 2-hydroxyethyl methacrylate, and one of its isomers is of the following formula:

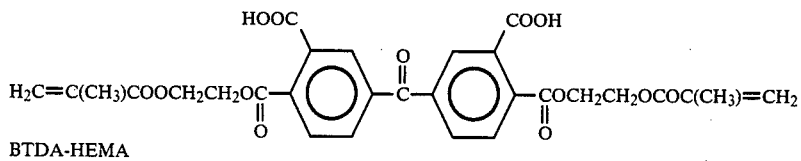

BTDA-HEMA

Preferably, the excess solution of PMDM and/or BTDA-HEMA is not removed, but rather, the solvent is removed by evaporation that may be speeded by applying a gentle stream of air at any feasible temperature.

Advantageously, the components necessary to effect the method of this invention may be packaged in an article of manufacture or "kit" for use by the dentist. As an illustration for the most preferred embodiment of the invention, such an article of manufacture would comprise the following: (a) two sealed cans, preferably containing an inert atmosphere, in which are provided glass cartridges stopped at each end with inert rubber plugs or stoppers and containing the first solution in one can and the second solution in the other can, and clearly marked as to which solution is contained therein. These cartridges and containers could be similar to ones used for dental anesthesia. The kit would also preferably contain one or more syringes for the anaerobic dispensing of the solutions. Most preferably, there would be a syringe for each of the types of solutions provided within the kit. These syringes would preferably be of metal or of some light-impervious material and would contain provision for the dispensing of the solutions in a controlled manner from disposable neeldes that could penetrate one of the rubber stoppers of the cartridge. Provisions should preferably be made to prevent inadvertent application of the solutions in the wrong order: for example, cartridges and syringes clearly marked "1" or "First" and "2" or "Second" and sized differently to prevent the cartridge from entering the wrong syringe.

The outer end of the needle preferably should be blunt to avoid any accidental penetration of soft tissue, and the needle should be curved to facilitate application of the liquids. Its purpose would be to apply the solution in a controlled manner to specific areas of teeth under treatment. The syringe would also provide for means of controlled pressure on the opposite stopper or plug of the cartridge and would preferably avoid features which might allow aspiration of air through the needle back into the cartridge space containing the solutions described hereinabove. An example of a suitable syringe for the dispensing of the treatment solutions of this invention would be the new improved Perio ® all stainless steel syringe supplied by the Universal Dental Implements, Inc., 98 James Street, Suite 101, Edison, NJ 08820, modified to reduce the quantity of liquid ejected. Other cartridges and syringes or modifications of existing cartridges and syringes used for dental anesthesia might be suitable and can be devised by those skilled in the art. By such means the treatment solutions can be prepared, stored, and dispensed anaerobically so that there will be adequate storage stability of these solutions from the time of manufacture to the time of utilization. The disposable needles can be changed between patients, the outer syringe can be sterilized between uses with different patients, and the inner cartridges used repeatedly until their contents of solutions are completely expended with no waste.

After the dentin, enamel, or other surface is prepared as described above, a mix of composite or unfilled resin may be applied. Adhesion tests utilizing extracted human teeth indicated strong adhesive bonding when utilizing the most preferred embodiments of the invention (Table 1). Although the formulations shown in this table do not necessarily represent optimized proportionalities of the ingredients, the data indicate that very strong adhesive bonding can be obtained with various proportions, concentrations, and recipes for the preparation of the solutions.

TABLE 1

Tensile Adhesive Strengths of a
Composite Bonded to Treated Surfaces
Dentin Surface Treatment

| Aqueous Solution Contents | Acetone Solution Contents | Average Adhesion psi | MPa |
|---|---|---|---|
| $2Al(NO_3)_3.3(C_2H_2O_4).5.4NPG(5.4\%)$ | PMDM | 1,960 | 13.5(3.4) |
| $2Al(NO_3)_3.3(C_2H_2O_4).4NPG(4\%)$ | PMDM | 1,740 | 12.0(4.6) |
| $2Al(NO_3)_3.3(C_2H_2O_4).2NPG(2\%)$ | PMDM | 1,510 | 10.4(4.0) |
| $Al_2(C_2O_4)_3 3.4\%.NPG.HNO_3(2.5\%)$ | PMDM | 1,450 | 10 |
| $Al_2(C_2O_4)_3 3.4\%.NPG.HNO_3(2.5\%)$ | PMDM. CQ 0.2% | 725 | 5 |
| $Al_2(C_2O_4)_3 3.4\%.NPG.HNO_3(1.5\%)$ | PMDM | 870 | 6 | where:
NPG = N—phenylglycine
psi = pounds per square inch
MPa = mega Pascals
Values are averages of 8 measurements (with standard deviations in parentheses).
CQ = camphoroquinone The table illustrates features and advantages of the most preferred embodiment, namely: aluminum ions can be substituted for ferric ions; a strong acid can be added as such ($HNO_3$) or as an acidic salt ($Al(NO_3)_3$); aluminum oxalate is soluble in the acidic solution; NPG can be incorporated into the essentially aqueous solution because of the low pH (which probably forms the cationic salt of NPG); the addition of camphoroquinone and subsequent exposure to bright light (which would assure the polymerization of the PMDM) does not increase the bond strength, suggesting that there is spontaneous polymerization of the PMDM even in the absence of a polyvalent cation capable of changing valence by unit steps (such as $Fe^{3+}/Fe^{2+}$); the new invention provides the manufacturer and dentist with two rather than three solutions, and eliminates a solvent-application step; and a polyvalent cation ($Al^{3+}$) which cannot discolor by the formation of a black sulfide (such as impure FeS and/or other iron pigments) under oral conditions is useful.

The average tensile bond strengths obtained by the most preferred embodiment of the invention are greater than the bond strengths of currently available commercial products. Table 2, which follows, gives bond strengths obtained by same test method when state-of-the-art commercial dentin adhesives are utilized with the same composite or the composite recommended by the manufacturer:

TABLE 2

Tensile Adhesive Strengths of Composites
Bonded to Treated Dentin Surfaces

| Dentin Surface Treatment Material | Average Adhesion* psi | MPa |
|---|---|---|
| Clearfil# | 870 | 6 |
| Scotchbond | 580 | 4 |
| Bondlite | 435 | 3 |
| Dentin Adhesit | 290 | 2 |
| J & J Dentin Bonding Agent | 145 | 1 |

*Average values for 8 measurements.
This technique calls for an acid etching of dentin, the nature of which most experts in the field do not consider safe for the dental pulp.

A distinction should be made with regard to the use on vital dentin of acids or acidic solutions which do or do not have "self-limiting" properties by forming insoluble precipitates within the dentinal tubules. It is considered very desirable that if an acidic solution is applied to vital dentin, it have some such mechanism for preventing the extensive opening and enlargement of dentinal tubules (as occurs with the Clearfil procedure).

The most preferred embodiment provides aluminum ions and oxalate ions which can, when reacting with the dentin substrate, produce precipitates of insoluble aluminum phosphate, "aluminum collagenate", and calcium oxalate; these provide the desired self-limiting characteristics by obturating the lumen of dentinal tubules, thereby protecting the odontoblasts and vital pulp tissues.

Other Embodiments of The Invention That Are Preferred But Not Most Preferred This aspect of the invention comprises materials and methods essentially the same as the foregoing, but divided into three separate application steps. By using extra application components, bond strengths equal to or perhaps higher than those of the preceding more preferred embodiments may be achieved, but the feasibility in dentistry is somewhat less because of the requirement of additional containers in the kits provided, additional application steps, and additional time required for utilization by the dentist or other end user. Treatment of the surface with a solution of aluminum nitrate and aluminum oxalate followed by a solution of NPG and then one of PMDM provides an example.

EXAMPLE 1

Commercial aluminum oxalate, analyzed to be approximately $Al_2(C_2O_4)_3.0.84\ C_2H_2O_4.10H_2O$ (0.491 grams), and commercial aluminum nitrate, $Al(NO_3)_3.9-H_2O$ (0.507 grams), and $H_2O$ (9.0 grams) were combined, yielding a solution in which there were aluminum ions stemming from oxalate and nitrate. The tooth surface was treated with this solution for sixty seconds, rinsed with water, and blown dry with air. After that, an NPG solution in acetone (10 w/w%) was applied for sixty seconds. The excess NPG was removed with a drop of clean acetone and the surface was then blown dry with air. Finally, a 5% acetone solution of PMDM was applied for sixty seconds and residual solvent was removed by blowing with a stream of air. After this, Adaptic ® was applied as before and after immersion in water the bond strengths were tested, yielding an average of 2,030 psi (s.d. 540), 14.0 MPa (n=8; s.d. 3.75). Similar treatment with these solutions yielded on enamel 1.580 psi (s.d. 800), 10.9 MPa (n=4; s.d.=5.5 MPa).

EXAMPLE 1A

To eight dentin surfaces was applied an aqueous ferric oxalate solution for 60 s. The surfaces were then washed with water and blown dry. Thereafter, a 10% aqueous solution of the amino acid glycine,

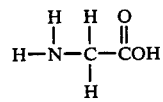

was applied for 60 s. After rinsing with water and drying with air, a 5% acetone solution of PMDM was applied and dried with an air stream. This average bond strength with Adaptic, as measured before, was 6.1 MPa (885 psi) with a s.d.=3.3 MPa (480 psi).

Other Embodiments of the Invention

Another aspect of the invention comprises the use of aqueous nitric acid solution followed by application of an acetone solution of an amino acid, for example, NPG or its analogs, and subsequently followed by the application of an acetone solution of a coupling agent, for example, PMDM or its analogs.

EXAMPLE 2

When a 2.5% $HNO_3$ solution was applied, washed, and dried followed by a 10% NTG-GMA acetone solution, followed by a drop of acetone, as described previously, and followed by a 5% acetone solution of PMDM, the bond strengths on dentin were 12.3 MPa with a standard deviation of 2.8 (n=16) and on enamel was 17.0 MPa with a standard deviation of 4.1 (n=8). When 3.4 wt% anhydrous ferric oxalate was additionally added to a 2.5% nitric acid solution as a first step, other steps being as just previously described, the bond strength to dentin was 11.7 MPa with 3.6 standard deviation, and the bond strength to enamel was 16.9 MPa with a standard deviation of 4.6.

The foregoing illustrates the discovery that strong bonding can be obtained with or without the polyvalent cation and the oligocarboxylic acid, but the latter two are preferred because of protective action with regard to pulp response under vital dentin surfaces.

Various acidic and chelating compound solutions can be used as the first step to remove the smeared or disturbed surface layers of dentin and/or smeared or contaminated surface layers of enamel.

More preferred than this, however, is the combination of nitric acid and an amino acid, e.g., NPG, in the same solution, followed by the application of a coupling agent, e.g., PMDM, as a second step. These embodiments may be preferred in industrial and nondental applications, but are less preferred for dentistry because they open and enlarge the dentinal tubules in vital dentin, allowing the PMDM or other coupling agent to penetrate and polymerize within the enlarged dentinal tubules. This is not deleterious from a bond-strength point of view, but it is not to be recommended over embodiments which incorporate aluminum (and/or other polyvalent cations) and/or oxalic acid and/or dibasic or polybasic carboxylic acids ("oligocarboxylic acids" as listed in U.S. Pat. No. 4,514,527).

As evidence for this assertion, a test method developed by Pashley, et al. (Journal of Dental Research, Volume 60, page 686, 1981), which is a measure of hydraulic conductance of fluids through dentinal tubules, was used to observe the effect of aluminum oxalate solution on the permeability of dentin. Using this test method, it was observed that the smear layer (disturbed surface layer formed by cutting the tooth) on the outer surface of the dentin specimen produced a liquid flow rate of about 4 minutes per cm which was slower than that which would have been observed if the outer surface had been acid etched with nitric acid, citric acid, or other simple acid, leading to a flow rate of about 1 minute per cm. By contrast, treatment with ferric oxalate or aluminum oxalate decreased the flow rate about 80-90% as compared with the unaltered smear layer.

Furthermore, scanning electron microscopy has shown that the addition of ferric oxalate to a solution of nitric acid has reduced the accessability of the dentinal tubules to the PMDM monomer: when 2.5% nitric acid was used, the PMDM penetrated deeply into the open dentinal tubules, whereas 2.5% nitric acid which also contained about 3 to 5% ferric oxalate prevented the penetration of the PMDM monomer into the tubules. In both cases, the adhesive bond strengths were high and of about the same average value. Therefore, until sufficient tests on experimental animals are conducted, it is recommended that the treatment solution contain not only nitric acid, but also a polyvalent cation and/or a dibasic or polybasic carboxylic acid ("an oligocarboxylic acid") when the embodiments of this invention are used with vital teeth of humans. The polyvalent cation and/or oligocarboxylic acid provide a "self-limiting" aspect to the depth of penetration in the case of dentin.

EXAMPLE 3

An aqueous solution containing $HNO_3$ and NPG or an aqueous solution containing the nitric acid salt of the NPG can be used as a first step, followed by the PMDM as a second step and the subsequent application of a composite resin to obtain strong adhesive bonding. For example, to a 2.5% w/w $HNO_3$ aqueous solution was added NPG, with NPG being equimolar to $HNO_3$. This solution was applied for 60 seconds to dentin surface, the surface was rinsed with water for 10 seconds, and blown with air for 10 seconds; then the acetone PMDM solution was applied as described previously. The average tensile bond strength for eight teeth was 11.4 MPa (s.d.=3.8). When the application of the $NPG.HNO_3$ solution was followed by washing with water and then acetone before drying and applying the PMDM, the average of eight measurements was 12.7 MPa (s.d.=5.2). When the procedure was further simplified by blowing away, with a forceful stream of air, the $NPG.HNO_3$ aqueous solution, followed immediately by application of the acetone solution of PMDM and composite, the same bond strength was obtained, namely 12.7 MPa (s.d.=4.3), there also being an average of eight measurements. When the concentration of the acidified NPG solution was lower, good results were also obtained: when 5 grams of a 2.5% $HNO_3$ solution was diluted with 3.33 g $H_2O$ (yielding a 1.5% $HNO_3$ solution) the addition of 0.3 g of NPG produced an acidified NPG solution of lower concentration. When this was used as described previously with no wash after its 60 second application (the solution being removed forceably with a stream of compressed air), the use of the PMDM solution and Adaptic® composite also gave high bond strengths, 13.2 MPa (s.d.=2.6; n=8). Other ratios or proportionalities of NPG or its analogs and $HNO_3$ or other suitable strong acids can be utilized providing that there is sufficient lowering of the pH to provide a water-soluble salt form of NPG or its analogs; also provided that there is sufficient acidity or sequestering capability by chelate complexation to bring about the required cleansing and alteration of the substrate surface; and also providing that there is sufficient amino acid present to serve as a coreactant with the PMDM applied subsequently so as to provide polymerization initiation of the PMDM or its analogs.

The aqueous solution can optionally contain compatible organic water-soluble solvents sufficient to maintain the compound or compounds and their strong acid salts in solution.

EXAMPLE 4

An example of an aqueous solution that can dissolve enamel and the mineral portion of dentin by action of a sequestering agent, ethylenediaminetetraacetic acid (EDTA), which is a compound containing amino groups and carboxyl groups, is as follows: aqueous 0.5 molar EDTA, neutralized to pH 7.4 by the formation of the partial sodium salt, was applied to dentin surfaces for 60 seconds. The EDTA solution was rubbed on the surface lightly with cotton pledget for about 30 seconds and then the solution was allowed to stand for the additional 30 seconds. The surface was then rinsed with distilled water for 10 seconds, blown with air for 10 seconds, and the 10% acetone solution of NPG was applied, followed by the PMDM solution and the composite as described previously. The average bond strength on dentin of eight teeth was 12.0 MPa (s.d.=3.6). With the same application of the EDTA solution, but with omission of the NPG solution, treatment with the PMDM and composite yielded an average of only 2.6 MPa (s.d.=2.0).

EXAMPLE 5

Other acids can be used in conjunction with NPG and PMDM. For example, an aquous solution of 35% $H_3PO_4$ (orthophosphoric acid) combined with 6% NPG was applied to dentin surfaces for 60 seconds, washed with water, blown with air, and then an acetone solution of PMDM was applied as before. The average of eight bond strength measurements was 11.0 MPa (s.d.=2.5).

EXAMPLE 6

An aqueous ferric oxalate solution containing a small amount of nitric acid was applied to eight dentin surfaces followed by washing, drying, and the application of the amino acid N-phenylalanine ("NPA" 10% in acetone) followed by the use of acetone to remove excess unbonded NPA amino acid, and subsequent treatment with a 5% acetone solution of PMDM coupling agent, and then Adaptic ® composite as described previously. The average bond strength was 16.3 MPa (s.d.=6.4).

Also considered to be within the scope of the present invention is the use of soluble salts containing various elements forming polyvalent cations. These may include; e.g., Al, Ti, V, Cr, Mn, Fe, Co, Ni, Cu, Zn, Ga, Ge, Y, Zr, Nb, Mo, Tc, Ru, Rh, Pd, In, Sn, Sb, Re, Os, Ir, Ce, Sm, Eu, Yb, Pa, and U. One or more cations of these elements may be used (with or without cations of other elements) together with one or more of the dibasic or polybasic carboxylic acids selected from the group including: dihydroxymaleic, diglycollic, oxalacetic, oxalic, malonic, succinic, glutaric, adipic, pimelic, suberic, azelaic, sebacic, malic, ethane-tetracarboxylic, phloinic, chloramalic, itaconic, citraconic, mesaconic, aconitic, citric, tartronic, chlorosuccinic, mesoxalic, tartaric, tricarballylic, acetone dicarboxylic, iso-citric, alpha-ketoglutaric, saccharic, mucic, talo-mucic, trihydroxyglutaric, phospho-glyceric, dimethyl malonic, N-phenyl-glycine-o-carboxylic, 1:2-cyclopropanedicarboxylic, cyclopropane-1:1:2-tricarboxylic, cyclobutane-1:1-dicarboxylic, cyclobutane-1:2-dicarboxylic, cylcobutane-1:3-dicarboxylic, cyclobutane-1:1:3:3-tetracarboxylic, alpha-truxillic, beta-isotruxillic, 2:3-diphenylbutane-1:1:4:4-tetracarboxylic, cyclo-pentane-1:1-dicarboxylic, cyclopentane-1:2-dicarboxylic, apo-camphoric, camphoric (d, 1 isomers), 2:5-dimethylcyclopentane-1:1-dicarboxylic, alpha,alpha'-di-sec.-butyl-glutaric, hexahydro-phthalic, hexahydro-terephthalic, hexahydro-isophthalic, beta-methyl-adipic, isopropyl-succinic, spiroheptane-carboxylic, alpha-tanacetogendicarboxylic, caronic, pinic, norpinic, methyl-succinic, trimethylsuccinic, 1:1-dimethyl-succinic, dehydrocamphoric, homocamphoric, apocamphoric, homoapocamphoric, methyl-nor-homocamphoric, iso-fenchocamphoric, alpha-hydroxyiso-fenchocamphoric, alpha,alpha,alpha'alpha'-tetramethyl glutaric, 1:2-dimethyl succinic, 1:1dimethyl-glutaric, dehydro-mucic (alpha,alpha'furan-dicarboxylic), o-carboxyphenylthioglycollic, furazan-dicarboxylic, 4:5-triazole-dicarboxylic, meconic, 3:4:5:6-pyridazine-tetracarboxylic, uroxanic, 1:3:5-triazine-2:4:6-tricarboxylic, chelidonic, meta-hemipinic, cinchomeronic, alpha-carbo-cinchomeronic, hydrastic, 3:4:5-trimethyoxy-1:2-phthalic, trimellitic, isophthalic, terephthalic, phthalic, 4-methoxy-phthalic acid, and lower-molecular-weight polyacrylic acid and copolymers of acrylic and polymerizable carboxylic acids. The foregoing acids are expressly defined for purposes of this invention as "oligocarboxylic acids." Aqueous, or mixed solvent solutions of these are applied to the substrate surface to which bonding is desired.

Water, solvents, or mixtures of water with other solvents are used to prepare solutions of these cations and anions. These cations and anions can be used together as complex mixtures so as to form adequately soluble salt solutions for the first step of the present method. After exposure of the surface to such solutions, for a suitable length of time and at a suitable temperature, the excess solution and soluble reaction products can be washed away with water or the same or a different solvent mixture to obtain the desired structure and chemical composition of an altered surface. Not all combinations of cations and anions may be efficacious (e.g., aqueous solutions of titanium oxalate, titanium fluoride and titanium potassium oxalate yielded poor results when substituted for ferric oxalate), and an oxidizing or reducing agent and/or a photoinitiating agent such as camphoroquinone with an amine or amino acid may be advantageously employed in some cases to facilitate the polymerization of the monomeric components such as PMDM and/or its analogs.

EXAMPLE 7

Two dentin surfaces were treated with an aqueous solution of pH 1.3 (703 mOsm) containing cupric cations and oxydiacetic (diglycollic) acid and sulfate anions; with an acetone solution of NTG-GMA; with an acetone solution of PMDM; then with a UV light. A composite resin bonded to these two surfaces with strengths of 1,480 and 1,920 psi, respectively; the dentin broke cohesively when the latter was tested.

Alternatively, the substrate surface may be acidified or treated with an acidic solution, e.g., with aqueous citric acid, in advance of application of the salt(s).

EXAMPLE 8

Dentin surfaces of 5 extracted teeth were treated with an isotonic citric acid solution; then with an aqueous solution containing cations of iron, copper, manganese, and cobalt, and anions of oxalic, citric, oxydiacetic, and tartaric acids, and ammonium ions. After rinsing with water and drying with an air stream, an acetone solution of NTG-GMA was then applied to the pretreated surfaces followed by an acetone solution of PMDM. A UV light was shined on the surfaces, and mixed composite resin was placed on each in the usual way. After immersion in water for one week the tensile adhesive bond strengths were found to average 2,400 psi. (16.5 MPa). In one of these, which broke at 3,230 psi, a piece of dentin was pulled out of the tooth surface when the bond broke.

EXAMPLE 9

Adhesive bonding to a proprietary metallic alloy containing and/or capable of binding metallic ions, used for both dental and industrial applications, was significantly stronger when the method of the present invention was used, compared to conventional procedures.

What is claimed is:

1. A method for preparing the surface of dentin, enamel, or other natural or industrial substrates containing or capable of binding metallic ions, for adhesion of composite materials or resins, which method comprises:
   (a) first contacting with the surface an aqueous solution or solutions comprising (1) at least one strong acid and (2) at least one compound selected from the group consisting of (1) N-phenylglycine, (2) the adduct of N (p-tolyl) glycine and glycidyl methacrylate, (3) the addition reaction product of N-phenylglycine and glycidyl methacrylate, and (4) other amino acids;
   (b) then contacting with the surface a solution comprising at least one monomer selected from the group consisting of (1) the addition reaction product of pyromellitic acid dianhydride and 2-hydroxyethyl methacrylate, (2) the addition reaction product of 3,3',4,4'-benzophenonetetracarboxylic dianhydride and 2-hydroxyethyl methacrylate, (3) 4-methacryloxyethyltrimellitic anhydride, and (4) other compounds containing at least one group or moiety capable of free radical polymerization and at least one aromatic ring or moiety containing electron-withdrawing substituents that do not interfere with free radical polymerization.

2. A method as in claim 1 wherein the concentration of the strong acid is from about 0.1% to about 50%.

3. A method as in claim 1 wherein the concentration of the strong acid is from about 2 to 5%.

4. A method as in claim 1 wherein the strong acid is nitric acid.

5. A method as in claim 1 wherein the strong acid is phosphoric acid.

6. A method as in claim 1 wherein the concentration of the solution comprising at least one compound selected from the group consisting of (1) N-phenylglycine, (2) the adduct of N(p-tolyl) glycine and glycidyl methacrylate, (3) the addition reaction product of N-phenylglycine and glycidyl methacrylate, and (4) other amino acids is from about 0.1% to a saturated solution.

7. A method as in claim 1 wherein the concentration of the monomer in the solution of subpart (b) is from about 0.1% to a saturated solution.

8. A method as in claim 1 wherein the solvent for the solution of subpart (b) is acetone.

9. A method as in claim 1 wherein the aqueous solution of subpart (a) contains compatible organic water-soluble solvents sufficient to maintain the compound or compounds and their strong acid salts in solution.

10. A method as in claim 1 wherein the strong acid is nitric acid and the compound of subpart (a)(2) is N-phenylglycine.

11. A method as in claim 1 wherein the compound of subpart (a)(2) is N-phenylalanine.

12. A method for preparing the surface of dentin, enamel, or other natural or industrial substrates containing or capable of binding metallic ions, for adhesion of composite materials or resins, which method comprises:
   (a) first contacting with the surface an aqueous solution or solutions comprising at least one strong acid;
   (b) then contacting with the surface a solution comprising a solvent and at least one compound selected from the group consisting of (1) N-phenylglycine, (2) the adduct of N(p-tolyl)glycine and glycidyl methacrylate, (3) the addition reaction product of N-phenylglycine and glycidyl methacrylate, and (4) other amino acids; and
   (c) then contacting with the surface a solution comprising at least one monomer selected from the group consisting of (1) the addition reaction product of pyromellitic acid dianhyride and 2-hydroxyethyl methcrylate, (2) the addition reaction product of 3,3',4,4'-benzophenonetetracarboxylic dianhydride and 2-hydroxyethyl methacrylate, (3) 4-methacryloxyethyltrimellitic anhydride, and (4) other compounds containing at least one group or moiety capable of free radical polymerization and at least one aromatic ring or moiety containing electron-withdrawing substituents that do not interfere with free radical polymerization.

13. A method as in claim 12 wherein the concentration of the strong acid is from about 0.1% to around 50%.

14. A method as in claim 12 wherein the concentration of the strong acid is from about 2 to 5%.

15. A method as in claim 12 wherein the strong acid is nitric acid.

16. A method as in claim 12 wherein the strong acid is phosphoric acid.

17. A method as in claim 12 wherein the concentration of the compound in subpart (b) in the solvent is from about 0.1% to a saturated solution.

18. A method as in claim 12 wherein the concentration of the solution of at least one monomer is from about 0.1% to a saturated solution.

19. A method as in claim 12 wherein the solvent for the solution of subpart (b) is acetone.

20. A method as in claim 12 wherein the solvent for the solution of subpart (c) is acetone.

21. A method for preparing the surface of dentin, enamel, or other natural or industrial substrates containing or capable of binding metallic ions, for adhesion of composite materials or resins, which method comprises:
   (a) first contacting with the surface an aqueous solution or solutions comprising (1) at least one strong acid or acidic salt, (2) at least one polyvalent cation, (3) at least one polyfunctional acid which can form relatively water-insoluble precipitates with calcium or polyvalent cations at pH values above that of the aqueous solution, and (4) at least one compound selected from the group consisting of (1) N-phenylglycine, (2) the adduct of N(p-tolyl) glycine and glycidyl methacrylate, (3) the addition reaction product of N-phenylglycine and glycidyl methacrylate, and (4) other amino acids;
   (b) then contacting with the surface a solution comprising at least one monomer selected from the group consisting of (1) the addition reaction product of pyromellitic acid dianhydride and 2-hydroxyethyl methacrylate, (2) the addition reaction product of 3,3',4,4'-benzophenonetetracarboxylic dianhydride and 2-hydroxyethyl methacrylate, (3) 4-methacryloxyethyltrimelliticanhydride, and (4) other compounds containing at least one group or moiety capable of free radical polymerization and at least one aromatic ring or moiety containing electron-withdrawing substituents that do not interfere with free radical polymerization.

22. A method as in claim 21 wherein the strong acid is nitric acid and its concentration is from about 0.1% to about 20%.

23. A method as in claim 21 wherein the strong acid is nitric acid and its concentration is from about 2 to 5%.

24. A method as in claim 21 wherein the polyvalent cation is selected from the group consisting of aluminum and ferric ions, used separately or together, and in concentration between about 0.00001% and saturation.

25. A method as in claim 24 wherein the concentration of aluminum and ferric ions is between about 1% and about 5%.

26. A method as in claim 21 wherein the polyfunctional acid is selected from the group consisting of oxalic, citric, pyruvic, tartaric, and other oligocarboxylic acids, used separately or in combinations, and in concentrations between about 0.0001% and saturation.

27. A method as in claim 26 wherein the concentration of polyfunctional acid is between about 1% and about 10%.

28. A method as in claim 21 wherein at least one compound of subpart (a)(4) is selected from the group consisting of N-phenylglycine, N(p-tolyl) glycine, N-phenylalanine, sarkosine, N-lauroylsarkosine, glycine, N,N-dimethylglycine, 3(N-phenyl) amino propionic acid, 3(N-p-tolyl) amino propionic acid, omega-amino fatty acids, N-substituted-omega-amino fatty acids, the addition reaction product of N-phenyl glycine and glycidyl reagents, the reaction product of N(substituted phenyl) glycine and glycidyl reagents, and other amino acids; and wherein such compound or compounds, used separately or in combinations, are used in concentrations between about 0.1% and saturation.

29. A method as in claim 28 wherein the concentration of the compound of subpart (a)(4) is between about 1% and about 10%.

30. A method as in claim 28 wherein the concentration of the compound of subpart (a)(4) is equal to or less than the normality of the strong acid of subpart (a)(1).

31. A method as in claim 1 wherein the substrate surface is a dentin surface or an enamel surface.

32. A method as in claim 12 wherein the substrate surface is a dentin surface or an enamel surface.

33. A method as in claim 21 wherein the substrate surface is a dentin surface or an enamel surface.

34. A structure comprising a composite material or resin bonded to a dentin or enamel surface which has been prepared by the method of claim 1.

35. A structure comprising a composite material or resin bonded to a dentin or enamel surface which has been prepared by the method of claim 12.

36. A structure comprising a composite material or resin bonded to a dentin or enamel surface which has been prepared by the method of claim 21.

37. A structure comprising a composite material or resin bonded to the surface of a natural or industrial substrate which has been prepared by the method of claim 1.

38. A structure comprising a composite material or resin bonded to the structure of a natural or industrial substrate which has been prepared by the method of claim 12.

39. A structure comprising a composite material or resin bonded to the surface of a natural or industrial substrate which has been prepared by the method of claim 21.

40. An article of manufacture comprising in combination;
(a) a first container containing a composition comprising (1) at least one strong acid and (2) at least one compound selected from the group consisting of (1) N-phenylglycine, (2) the adduct of N(p-tolyl) glycine and glycidyl methacrylate, (3) the addition reaction product of N-phenylglycine and glycidyl methacrylate, and (4) other amino acids; and
(b) a second container containing a composition comprising at least one monomer selected from the group consisting of (1) the addition reaction product of pyromellitic acid dianhydride and 2-hydroxyethyl methacrylate, (2) the addition reaction product of 3,3',4,4'-benzophenonetetracarboxylic dianhydride and 2-hydroxyethyl methacrylate, (3) 4-methacryloxyethyltrimellitic anhydride, and (4) other compounds containing at least one group or moiety capable of free radical polymerization and at least one aromatic ring or moiety containing electron-withdrawing substituents that do not interfere with free radical polymerization;
said first and second containers being packaged together in said article of manufacture.

41. An article of manufacture as in claim 40 wherein the contents of the first and second containers are in solutions.

42. An article of manufacture comprising in combination:
(a) a first container containing at least one strong acid;
(b) a second container containing at least one compound selected from the group consisting of (1)N-phenylglycine, (2) the adduct of N(p-tolyl) glycine and glycidyl methacrylate, (3) the addition reaction product of N-phenylglycine and glycidyl methacrylate, and (4) other amino acids;
(c) a third container at least one monomer selected from the group consisting of (1) the addition reaction product of pyromellitic acid dianhydride and 2-hydroxyethyl methacrylate, (2) the addition reaction product of 3,3',4,4'-benzophenonetetracarboxylic dianhydride and 2-hydroxyethyl methacrylate, (3) 4-methacryloxyethyltrimellitic anhydride, and (4) other compounds containing at least one group or moiety capable of free radical polymerization and at least one aromatic ring or moiety containing electron-withdrawing substituents that do not interfere with free radical polymerization;
said first and second and third containers being packaged together in said article of manufacture.

43. An article of manufacture as in claim 42 wherein the contents of the first, second and third containers are in solutions.

44. An article of manufacture comprising in combination:
(a) a first container containing (1) at least one strong acid or acidic salt, (2) at least one polyvalent cation, (3) at least one polyfunctional acid which can form relatively water-insoluble precipitates with calcium or polyvalent cations at pH values above that of the aqueous solution, and (4) at least one compound selected from the group consisting of (1) N-phenylglycine, (2) the adduct of N(p-tolyl) glycine and glycidyl methacrylate, (3) the addition reaction product of N-phenylglycine and glycidyl methyacrylate, and (4) other amino acids; and (b) a second container containing at least one monomer selected from the group consisting of (1) the addition reaction product of pyromellitic acid dianhydride and 2-hydroxyethyl methacrylate, (2) the addition reaction product of 3,3',4,4'-benzophenonetetracarboxylic dianhydride and 2-hydroxyethyl methacrylate, (3) 4-methacryloxyethyltrimellitic anhydride, and (4) other compounds containing at least one group or moiety capable of free radical polymerization and at least one aromatic ring or moiety containing electron-withdrawing substituents that do not interfere with free radical polymerization;

said first and second containers being packaged together in said article of manufacture.

45. An article of manufacture as in claim 44 wherein the contents of the first and second containers are in solution.

46. An article of manufacture comprising in combination:

(a) a first container containing an acidic aqueous solution of aluminum nitrate, oxalic acid, and N-phenylglycine; and (b) a second container containing an acetone solution of PMDM;

said first and second containers being packaged together in said aritcle of manufacture.

* * * * *

UNITED STATES PATENT AND TRADEMARK OFFICE
CERTIFICATE OF CORRECTION

PATENT NO.    :   4,659,751
DATED         :   April 21, 1987
INVENTOR(S)   :   Rafael L. Bowen It is certified that error appears in the above-identified patent and that said Letters Patent is hereby corrected as shown below:

In the Title:

First line, "Obtained" should be "Obtaining".

In the Specification:

Col. 2, line 39, "material" should be "materials".

Col. 5, line 59, "cylindeers should be "cylinders".

Col. 12, line 46, "1.580" should be "1,580".

In the Claims:

Col. 18, line 14, "dianhyride" should be "dianhydride".

Signed and Sealed this

Eighth Day of December, 1987

*Attest:*

DONALD J. QUIGG

*Attesting Officer*    *Commissioner of Patents and Trademarks*